[12] United States Patent
Abel et al.

(10) Patent No.: US 9,686,623 B2
(45) Date of Patent: Jun. 20, 2017

(54) MIDDLE EAR IMPLANT

(75) Inventors: Eric William Abel, Dundee (GB);
David Ernest Young, Cambridgeshire
(GB); Robin Christopher Brodie,
Dundee (GB)

(73) Assignee: Sentient Medical Limited, Dundee (GB)

( * ) Notice: Subject to any disclaimer, the term of this patent is extended or adjusted under 35 U.S.C. 154(b) by 933 days.

(21) Appl. No.: 12/599,530

(22) PCT Filed: May 12, 2008

(86) PCT No.: PCT/GB2008/050344
§ 371 (c)(1),
(2), (4) Date: Apr. 5, 2011

(87) PCT Pub. No.: WO2008/139225
PCT Pub. Date: Nov. 20, 2008

(65) Prior Publication Data
US 2012/0016180 A1    Jan. 19, 2012

(30) Foreign Application Priority Data
May 11, 2007 (GB) .................................. 0709072.3

(51) Int. Cl.
*H04R 25/00* (2006.01)
*H04R 17/00* (2006.01)
*A61F 2/18* (2006.01)

(52) U.S. Cl.
CPC ........... *H04R 25/606* (2013.01); *H04R 17/00* (2013.01); *A61F 2002/183* (2013.01)

(58) Field of Classification Search
CPC .... H04R 25/60; H04R 25/604; H04R 25/606;
H04R 2225/63; H04R 2225/77; H04R
17/00–17/10; A61F 2002/183
(Continued)

(56) References Cited

U.S. PATENT DOCUMENTS 2,394,569 A    2/1946   Strommen
3,594,514 A    7/1971   Wingrove
(Continued)

FOREIGN PATENT DOCUMENTS

CN    1922402 A    2/2007
CN    1937970 A    3/2007
(Continued)

OTHER PUBLICATIONS

First Notification of Office Action issued by the State Intellectual Property Office of China on Feb. 22, 2012, which corresponds to Chinese Patent Application No. 200880022869.9, and is related to U.S. Appl. No. 12/599,530 with English translation.
(Continued)

*Primary Examiner* — Charles A Marmor, II
*Assistant Examiner* — Thaddeus Cox
(74) *Attorney, Agent, or Firm* — Studebaker & Brackett PC

(57) ABSTRACT

A hearing actuator (10) for implantation in the middle ear of a user. The actuator comprises transducer means (for example a piezoelectric device) (12) for converting electrical input signals into mechanical vibrations, and attachment means (16) for attaching one end of the transducer means to a first part of the middle ear. The actuator also comprises contacting means (14) which extends from an opposite end of the transducer means such that a longitudinal axis of the contacting means is substantially parallel to a longitudinal axis of the transducer means. The contacting means is for contacting a second part of the middle ear (to which it may be attached), so as to transmit the mechanical vibrations of the transducer means thereto.

22 Claims, 10 Drawing Sheets

(58) Field of Classification Search
USPC .............................................. 600/25; 607/57
See application file for complete search history.

(56) References Cited

U.S. PATENT DOCUMENTS

| | | | |
|---|---|---|---|
| 3,764,748 | A | 10/1973 | Branch et al. |
| 4,118,599 | A | 10/1978 | Iwahara et al. |
| 4,139,728 | A | 2/1979 | Haramoto et al. |
| 4,219,696 | A | 8/1980 | Kogure et al. |
| 4,624,672 | A | 11/1986 | Lenkauskas |
| 4,729,366 | A | 3/1988 | Schaefer |
| 4,759,070 | A | 7/1988 | Voroba et al. |
| 4,774,515 | A | 9/1988 | Gehring |
| 4,809,708 | A | 3/1989 | Geisler et al. |
| 4,845,688 | A | 7/1989 | Butler |
| 4,901,353 | A | 2/1990 | Widin |
| 4,957,478 | A | 9/1990 | Maniglia |
| 5,173,944 | A | 12/1992 | Begault |
| 5,233,665 | A | 8/1993 | Vaughn et al. |
| 5,279,292 | A | 1/1994 | Baumann et al. |
| 5,303,306 | A | 4/1994 | Brillhart et al. |
| 5,325,436 | A | 6/1994 | Soli et al. |
| 5,434,924 | A | 7/1995 | Jampolsky |
| 5,436,975 | A | 7/1995 | Lowe et al. |
| 5,456,654 | A | 10/1995 | Ball |
| 5,707,338 | A * | 1/1998 | Adams et al. .................. 600/25 |
| 5,825,894 | A | 10/1998 | Shennib |
| 5,879,283 | A | 3/1999 | Adams et al. |
| 5,913,815 | A | 6/1999 | Ball et al. |
| 5,984,859 | A * | 11/1999 | Lesinski .......................... 600/25 |
| 5,997,466 | A * | 12/1999 | Adams ................. H04R 25/606 |
| | | | 600/25 |
| 6,001,129 | A | 12/1999 | Bushek et al. |
| 6,137,889 | A | 10/2000 | Shennib et al. |
| 6,217,508 | B1 * | 4/2001 | Ball et al. ........................ 600/25 |
| 6,241,767 | B1 | 6/2001 | Stennert et al. |
| 6,261,224 | B1 | 7/2001 | Adams et al. |
| 6,267,731 | B1 * | 7/2001 | Kroll et al. .................... 600/559 |
| 6,315,710 | B1 | 11/2001 | Bushek et al. |
| 6,325,755 | B1 | 12/2001 | Bushek et al. |
| 6,364,825 | B1 | 4/2002 | Kennedy et al. |
| 6,398,717 | B1 | 6/2002 | Leysieffer et al. |
| 6,482,144 | B1 | 11/2002 | Muller |
| 6,537,199 | B1 * | 3/2003 | Muller et al. .................... 600/25 |
| 6,537,200 | B2 | 3/2003 | Leysieffer et al. |
| 6,629,922 | B1 * | 10/2003 | Puria ................... H04R 25/606 |
| | | | 381/312 |
| 6,671,559 | B2 | 12/2003 | Goldsmith et al. |
| 6,717,333 | B2 | 4/2004 | Hermle et al. |
| 6,875,166 | B2 | 4/2005 | Kroll et al. |
| 7,289,639 | B2 | 10/2007 | Abel et al. |
| 2001/0031908 | A1 * | 10/2001 | Buschek et al. ................ 600/25 |
| 2003/0097178 | A1 | 5/2003 | Roberson et al. |
| 2003/0130734 | A1 * | 7/2003 | Antonelli .................. A61F 2/18 |
| | | | 623/10 |
| 2005/0165481 | A1 | 7/2005 | Steinhardt et al. |
| 2007/0021833 | A1 | 1/2007 | Awengen et al. |
| 2007/0055372 | A1 * | 3/2007 | Prescott .................... A61F 2/18 |
| | | | 623/10 |
| 2008/0065002 | A1 | 3/2008 | Lobl et al. |
| 2008/0107546 | A1 | 5/2008 | Falch et al. |
| 2008/0208337 | A1 | 8/2008 | Awengen et al. |
| 2009/0023976 | A1 | 1/2009 | Cho et al. |
| 2009/0043149 | A1 | 2/2009 | Abel |
| 2009/0131742 | A1 | 5/2009 | Cho et al. |
| 2012/0016180 | A1 | 1/2012 | Abel et al. |

FOREIGN PATENT DOCUMENTS

| | | |
|---|---|---|
| DE | 2844979 A1 | 4/1980 |
| DE | 3508830 A1 | 9/1986 |
| DE | 29701534 U1 | 3/1997 |
| DE | 202007017910 U1 | 3/2008 |
| EP | 1498088 A2 | 1/2005 |
| JP | S60-154800 A | 8/1985 |
| JP | S62-277955 A | 12/1987 |
| JP | H06-339489 A | 12/1994 |
| JP | 2001-507964 A | 6/2001 |
| JP | 2008-526416 A | 7/2008 |
| RU | 2 096 027 C1 | 11/1997 |
| WO | 92/18066 A1 | 10/1992 |
| WO | 97/23117 A1 | 6/1997 |
| WO | 97/32385 A | 9/1997 |
| WO | 99/63785 A | 12/1999 |
| WO | 00/76271 A1 | 12/2000 |
| WO | 2006/075169 A | 7/2006 |
| WO | WO 2006075169 A1 * | 7/2006 |
| WO | 2008/139225 A2 | 11/2008 |

OTHER PUBLICATIONS

Second Notification of Office Action issued by the State Intellectual Property Office of China on Dec. 6, 2012, which corresponds to Chinese Patent Application No. 200880022869.9, and is related to U.S. Appl. No. 12/599,530 with English translation.

Japanese Office Action "Notice of Reasons for Rejection" dated Dec. 25, 2012, which corresponds to Japanese Patent Application No. 2010-507007 and is related to U.S. Appl. No. 12/599,530 with English translation.

The Examination Report issued by the New Zealand Intellectual Property Office on Apr. 11, 2011, which corresponds to New Zealand Patent Application No. 581738 and is related to U.S. Appl. No. 12/599,530.

The Examination Report under Section 18(3) issued by the Great Britain Intellectual Property Office on Apr. 18, 2011, which corresponds to GB Patent Application No. 0709072.3 and is related to U.S. Appl. No. 12/599,530.

An Office Action issued by the Canadian Intellectual Property Office on Aug. 22, 2013, which corresponds to Canadian Patent Application No. 2,594,761 and is related to U.S. Appl. No. 12/599,530.

An Office Action issued by the Japanese Patent Office on Sep. 25, 2013, which corresponds to Japanese Patent Application No. 2010-507007 and is related to U.S. Appl. No. 12/599,530.

Notice of Allowance issued by the Australian Patent Office on Aug. 16, 2013, which corresponds to Australian Patent Application No. 2008222478 and is related to U.S. Appl. No. 12/599,530.

The forth Notification of Office Action issued by the State Intellectual Property Office of China on Nov. 22, 2013, which corresponds to Chinese Patent Application No. 200880014635.X and is related to U.S. Appl. No. 12/599,530; with English language translation.

Leiner, et al.; "A Pathway for Information Transmission to the Inner Ear Application to Cochlear Implants"; ASAIO Journal 1992; 38: pp. M253-M256.

An Office Action issued by the Government of India Patent Office on Jun. 24, 2013, which corresponds to Indian Patent Application No. 1102/MUMNP/2007 and is related to U.S. Appl. No. 12/599,530.

The Japanese Office Action "Notice of Reason for Rejection" dated Jan. 10, 2012, which corresponds to Japanese Patent Application No. 2007-550843 and is related to U.S. Appl. No. 11/795,137 with translation.

The communication pursuant to Article 94(3) EPC dated Feb. 3, 2009, which corresponds to EP Application No. 06 700 906.8-2320 and is related to U.S. Appl. No. 11/795,137.

The Russian Office Action "Enquiry" dated Dec. 22, 2009, which corresponds to Russian Patent Application No. 2007131471/14(034299) and is related to U.S. Appl. No. 11/795,137 with translation.

The Canadian Office Action dated Oct. 1, 2012, which corresponds to Canadian Patent Application No. 2,594,761 and is related to U.S. Appl. No. 11/795,137.

The Australian Office Action dated Jan. 25, 2013, which corresponds to Australian Patent Application No. 2008249763 and is related to U.S. Appl. No. 11/795,137.

European Office Action issued on Aug. 22, 2013, which corresponds to EP08709667.3-1662 and is related to U.S. Appl. No. 11/795,137.

(56) References Cited

OTHER PUBLICATIONS

Japanese Office Action issued on Jul. 16, 2013, which corresponds to JP2009-552280 and is related to U.S. Appl. No. 11/795,137; with translation.
Canadian Office Action issued on Jul. 18, 2013, which corresponds to Canadian Patent Application No. 2,724,137 and is related to U.S. Appl. No. 11/795,137.
"First Notification of Office Action" issued by the State Intellectual Property Office of China on Jan. 28, 2014, which corresponds to Chinese Patent Application No. 201080032713.6 and is related to U.S. Appl. No. 12/599,530; with English language translation.
"First Notification of Office Action" issued by the State Intellectual Property Office of China on Feb. 27, 2014, which corresponds to Chinese Patent Application No. 201080032735.2 and is related to U.S. Appl. No. 12/599,530; with English language translation.
An Office Action issued by the Canadian Patent Office on Dec. 13, 2013, which corresponds to Canadian Patent Application No. 2,717,361 and is related to U.S. Appl. No. 12/599,530.
An Office Action; "Notice of Reasons for Rejection," issued by the Japanese Patent Office on May 27, 2014, which corresponds to Japanese Patent Application No. 2012-516862 and is related to U.S. Appl. No. 12/599,530; with English language translation.
Guiseppe Gastaldi; "International Search Report"; PCT/GB2008/050344; Apr. 7, 2009.
Guiseppe Gastaldi; "Written Opinion of the International Search Authority"; PCT/GB2008/050344; Apr. 7, 2009.

* cited by examiner

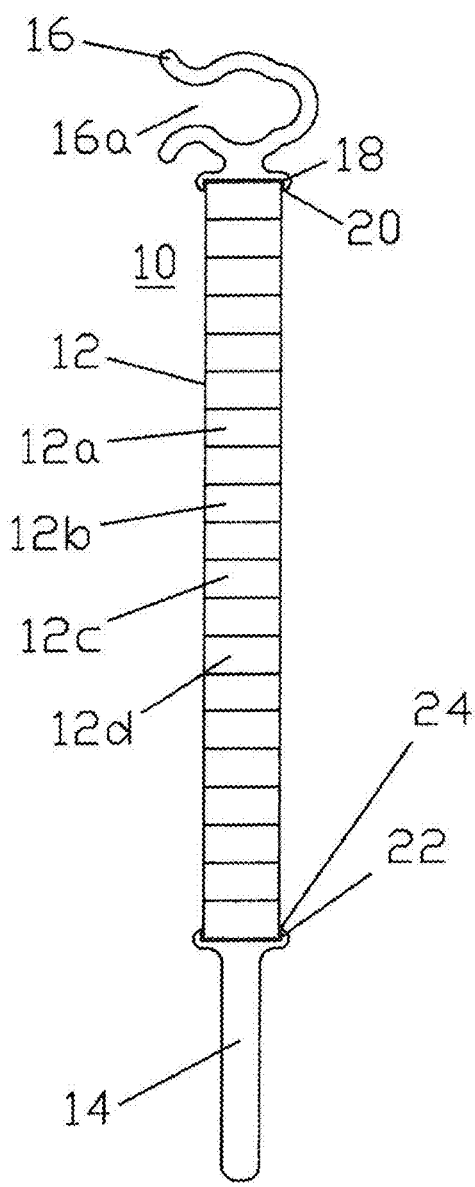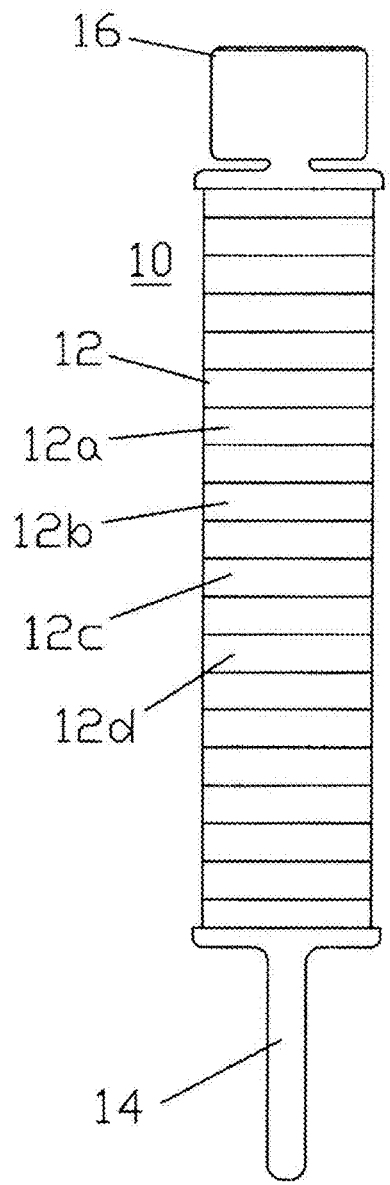

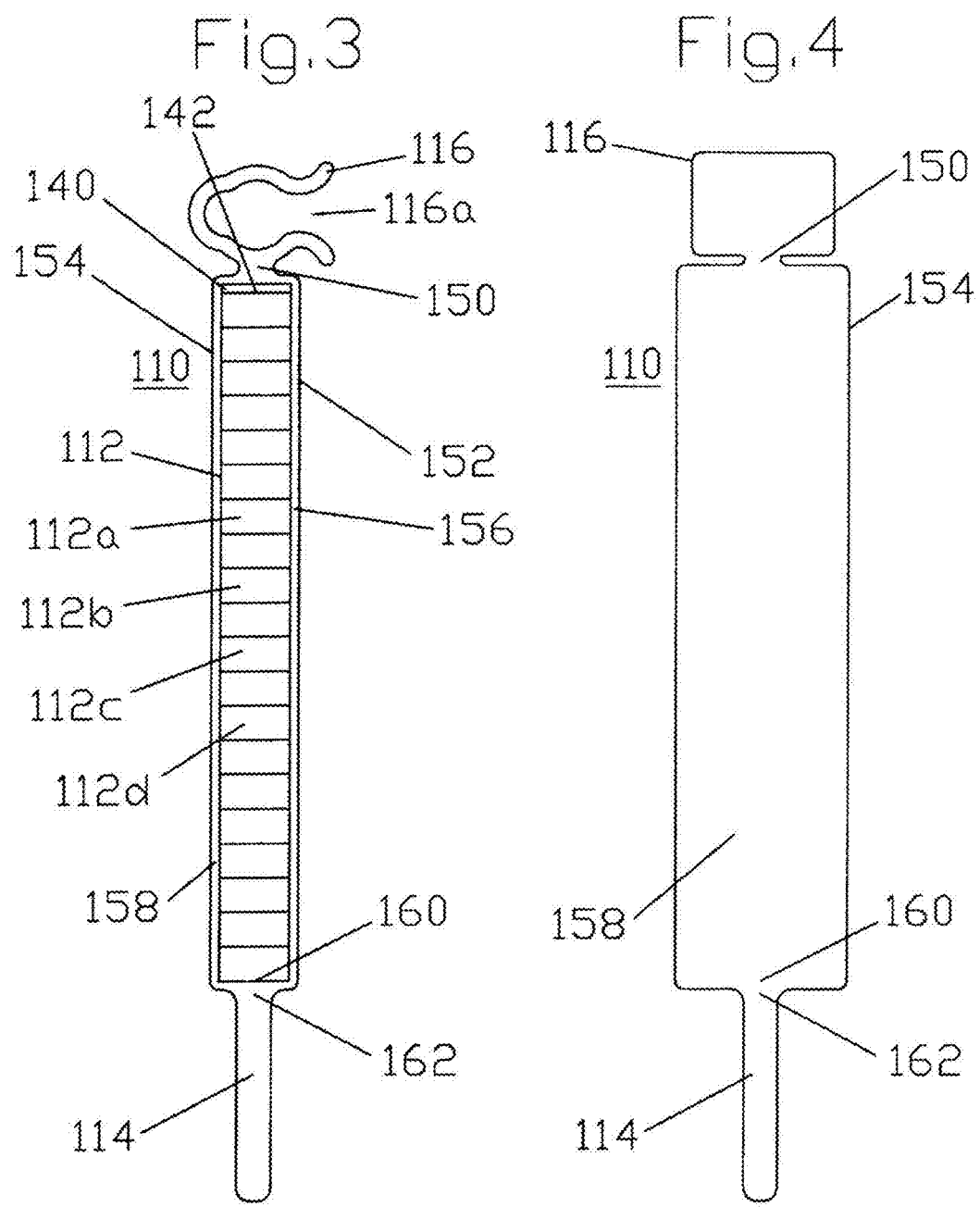

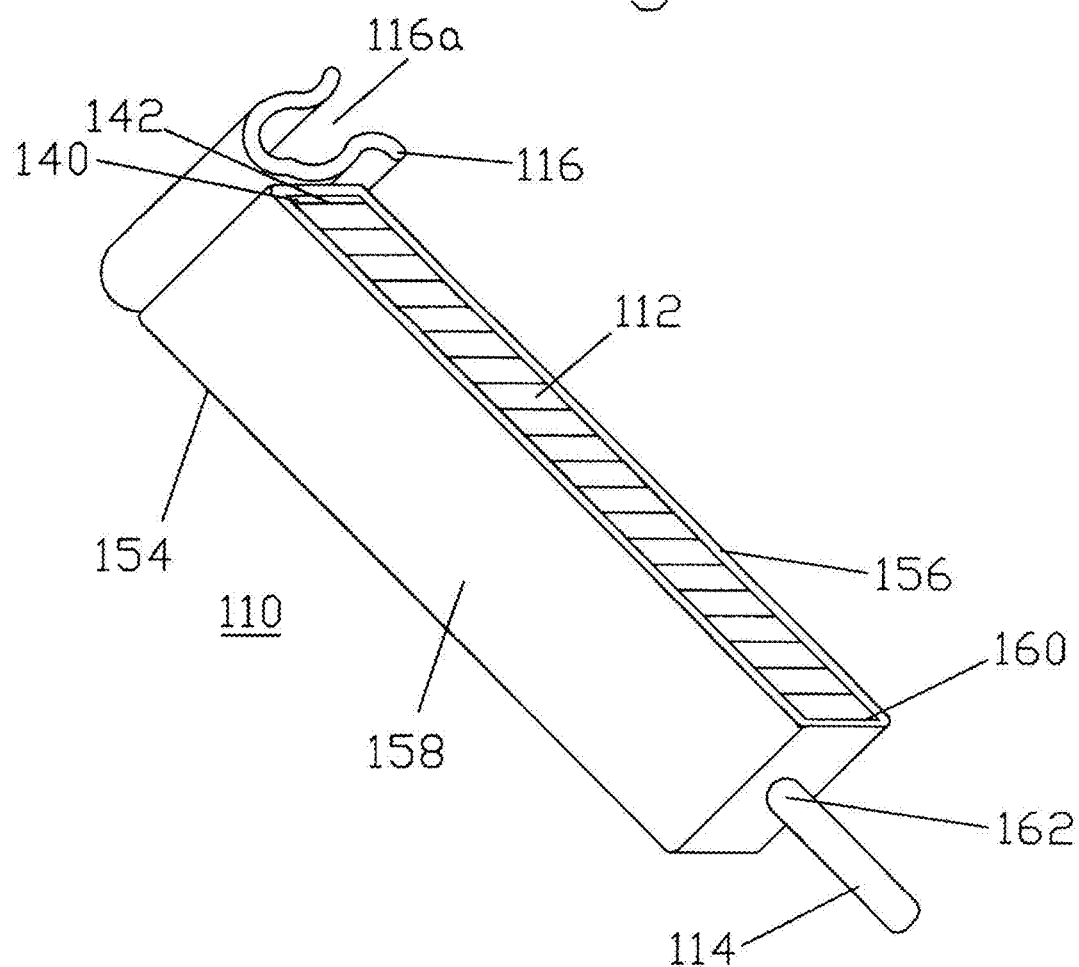

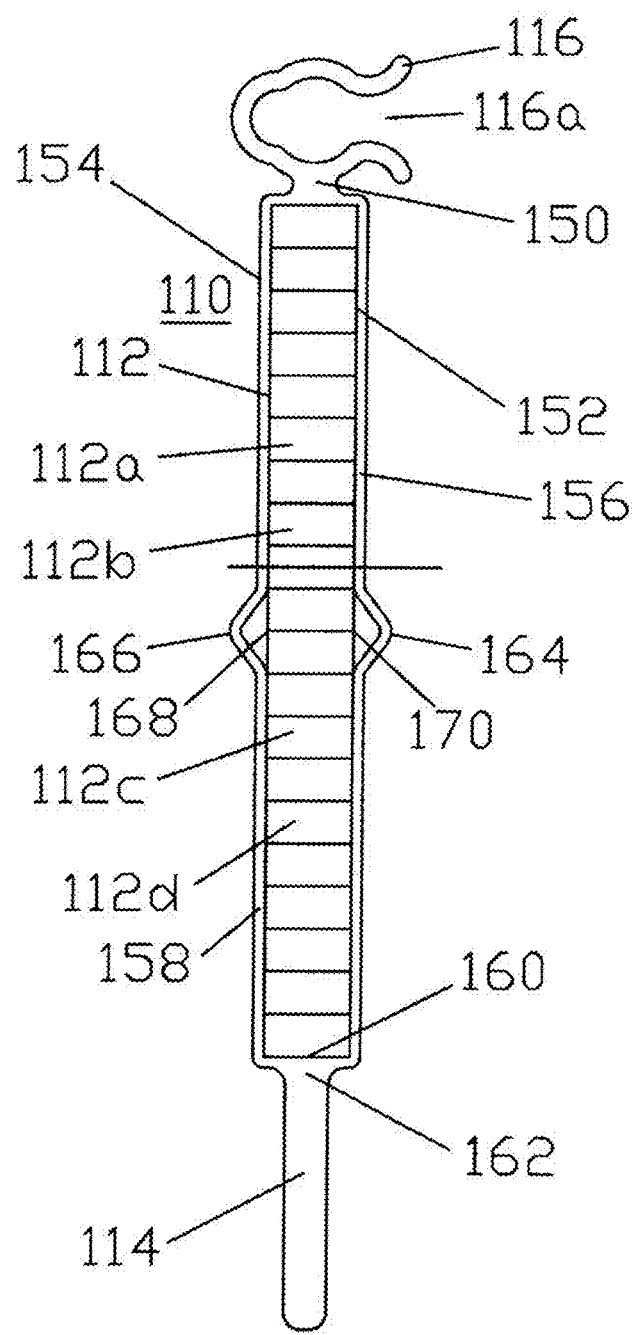

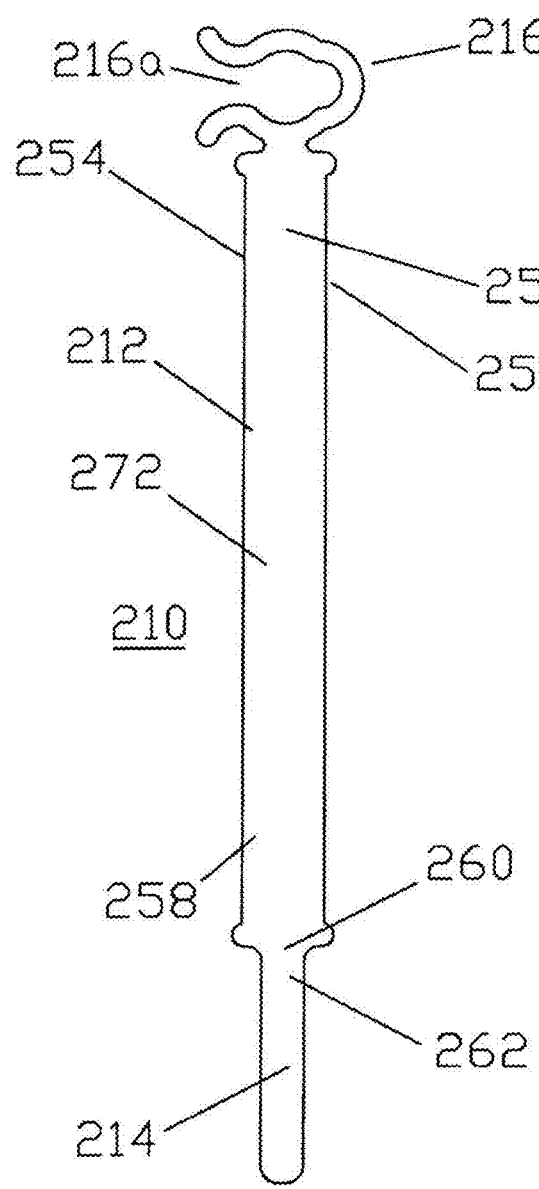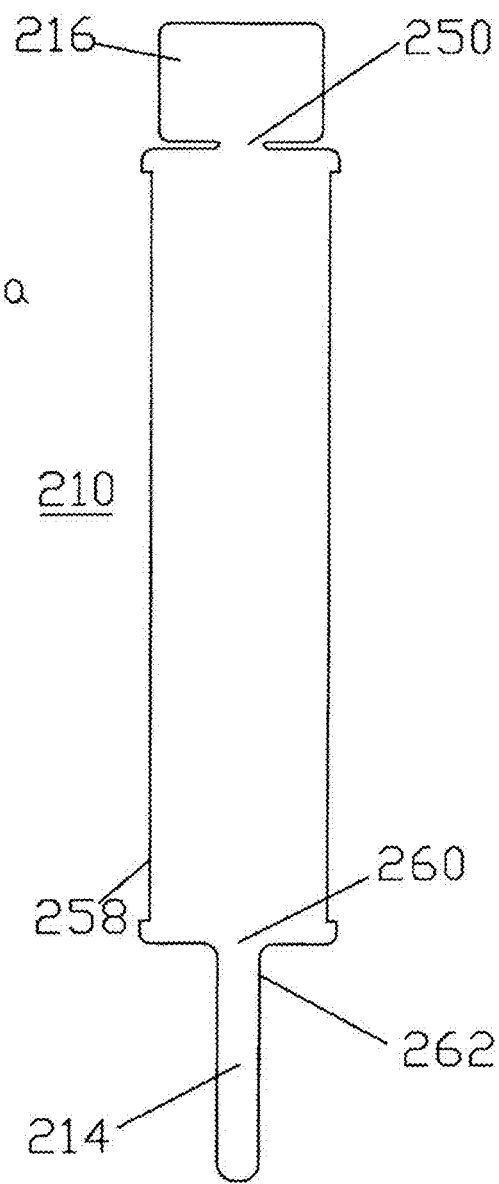

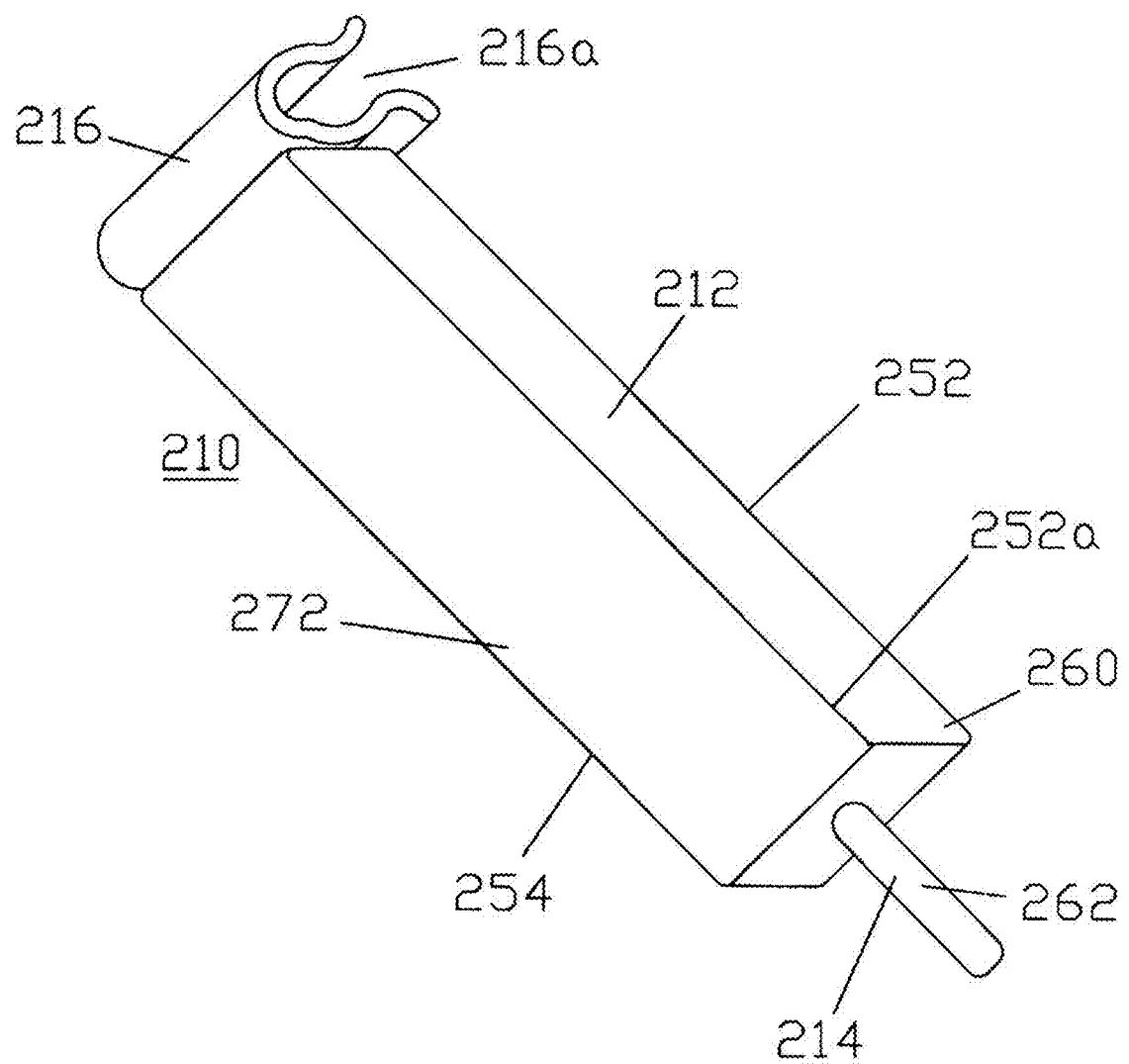

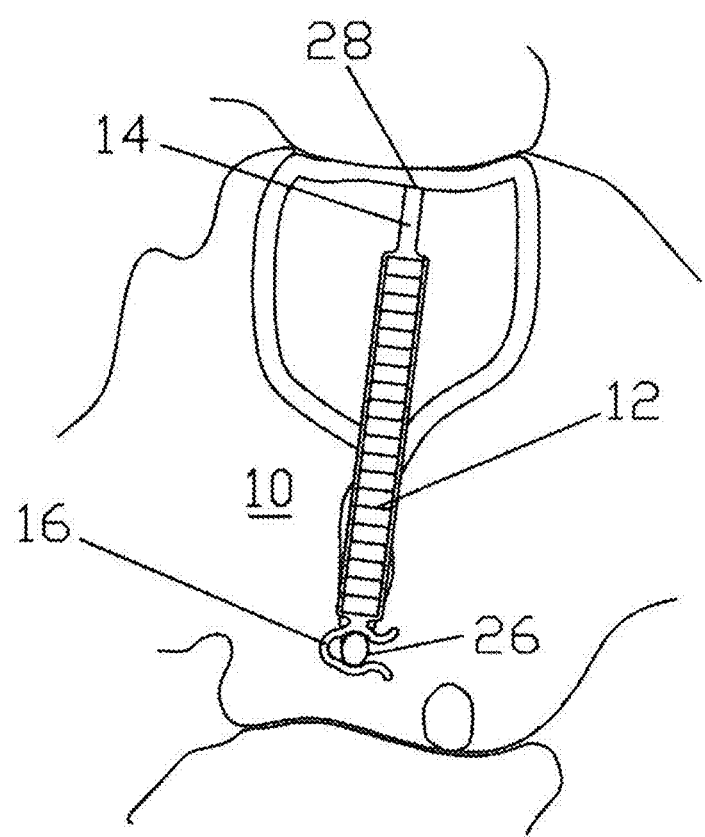

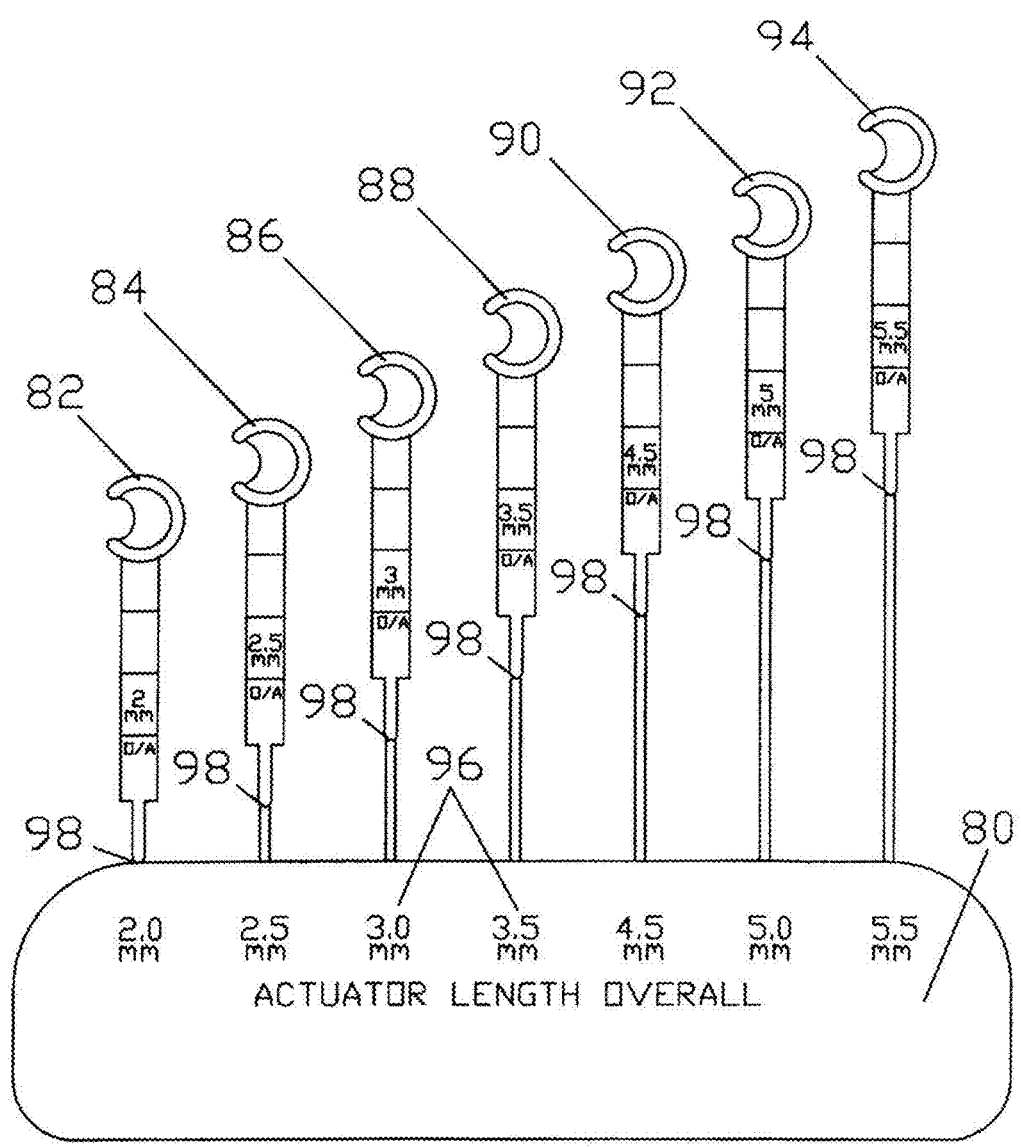

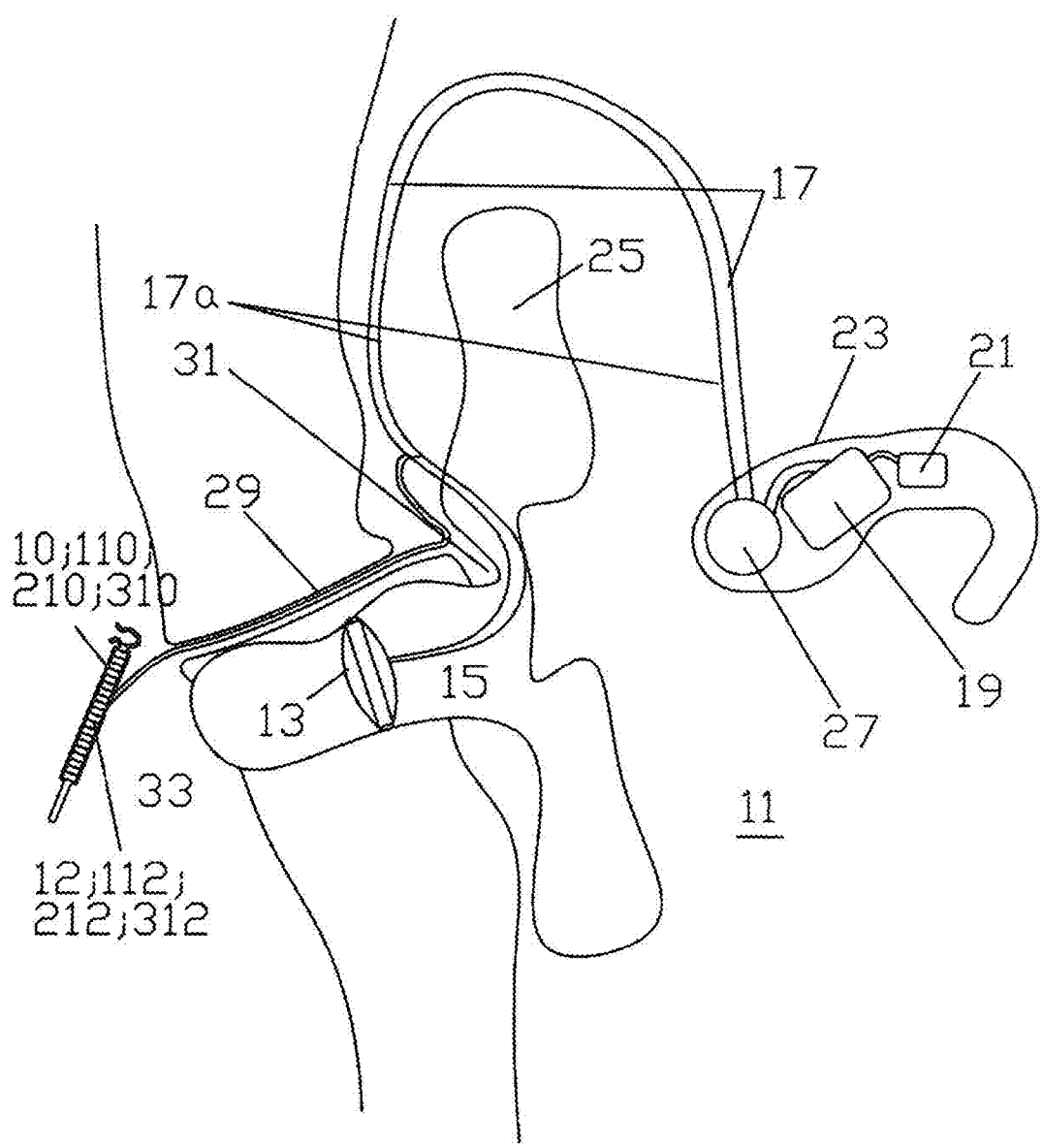

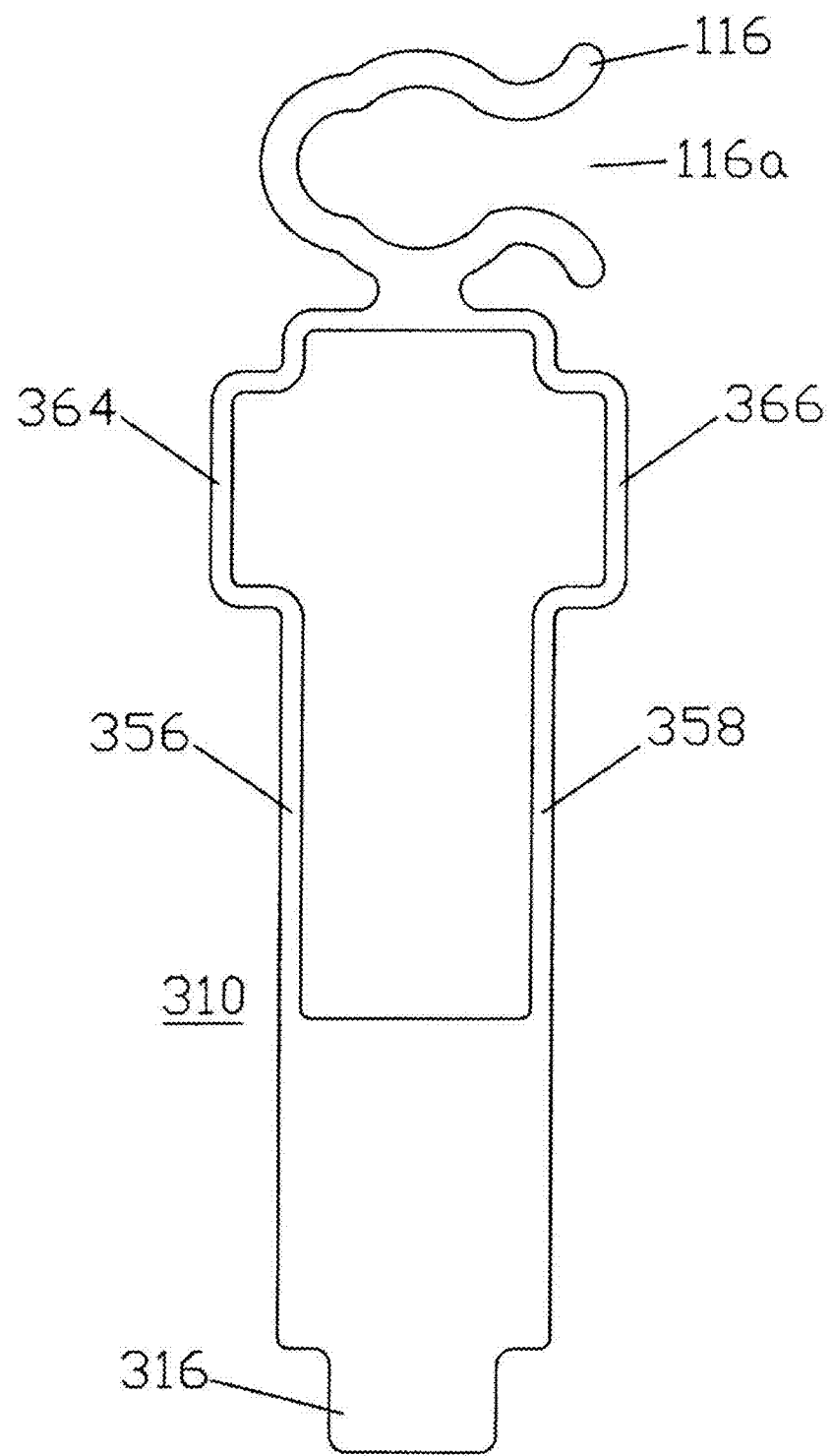

MIDDLE EAR IMPLANT

The present invention relates to devices for aiding the hearing impaired. More specifically the present invention relates to the provision of electromechanical actuators which can be directly attached to the ossicular chain of the middle ear for amplifying vibrations generated by sound signals.

Deafness affects 9 million people in the United Kingdom, of which over 80% have Sensorineural Deafness (SD). This debilitating condition afflicts about 10% of the population of the western world. There are several causes and the ageing process is very important with a significant proportion of those affected being over 60 years old. Hearing impairment is the third most common chronic problem affecting the ageing population—and one of the least diagnosed. There is also an increased prevalence in some sections of the younger age group, due to exposure to loud noise.

There are currently no effective means of repairing the cochlea or the nervous pathways to the brain. For most patients hearing can be restored adequately by sufficient amplification of sound with a hearing aid but middle ear implants (MEIs) provide mechanical amplification by vibrating the ossicular chain and up to 50% of all people with moderate to severe sensorineural hearing loss could potentially be treated more effectively with these implantable devices.

Middle ear implants can utilise actuators in the form of electromechanical displacement devices, that control the position of a component through the use of an electric field. In this regard, piezoelectric actuators are known and are based on the piezoelectric effect, whereby certain crystalline materials exhibit the property of changing shape when subjected to an externally applied voltage.

Many types of piezoelectric actuator have been proposed, especially since the nineteen-fifties and, these are now described by those skilled in the art according to a series of classes defined by shape (Brigham and Royster, 1969). There were originally five classes but at least seven classes are now generally accepted. It is well known to those skilled in the art that minor changes in the design of actuators which may be generally similar in appearance can make highly significant differences to performance and even feasibility of use for a particular application.

Middle ear implants with actuators based on the use of piezoelectric or electromagnetic transducers have been proposed. Actuators utilising piezoelectric transducers have the potential benefit of providing mechanical movement directly from an electrical signal to vibrate the ossicular chain as desired. Such actuators comprising piezoelectric transducers made from lead zirconate titanate (PZT) have been used in different configurations to provide assistance to the hearing impaired.

In U.S. Pat. No. 6,629,922 to Puria et al the authors describe a flextensional actuator for surgically implantable hearing aids wherein a piezo element is disposed between two end caps which function as flextensional amplifiers and these three components are glued together with suitable adhesive means. The authors refer to the actuator as a prismatoid type, however, it conforms with the widely accepted description of a cymbal actuator; a point which is conceded in several parts of the description, for example, with respect to their FIG. 4F. The authors contemplate encasing the actuator in biocompatible material to isolate it from the body.

In published PCT Application WO 2006/075169, the authors describe an actuator having a multi-layer piezoelectric stack and a frame component comprising at least one flextensional amplifier element and also having integral first and second end portions integral with and disposed substantially at right angles to the main plane of the flextensional amplifier or amplifiers.

With the present invention there is provided a middle ear implant in the form of an actuator for an implantable hearing aid system which may comprise a stack of piezoelectric elements each being by way of non-limiting example approximately 0.4 sq mm in cross section and preferably made from lead zirconate titanate (PZT) and arranged by way of non-limiting example in d33 configuration. This actuator, when used alone and driven with a suitable input voltage, which may typically be from 5-20V is capable of producing levels of amplification which can match or exceed those achieved with prior art actuators.

The actuator may be provided with attachment means, for attachment to, for example, at least one ossicle of the ossicular chain, preferably but not necessarily the incus long process. Attachment means are preferably in the form of clip means designed to provide constant loading means on the incus such that applied loads do not reach a level at which necrosis might be induced. Such a clip may be constructed from alloys such as nitinol according to designs which take account of the superelastic property of that material. The clip attachment means may be fixedly attached to the actuator by adhesive means.

The inventors also contemplate several alternative sites for the attachment of attachment means for the actuator of the present invention within the middle ear cavity. For instance, the actuator may be attached to sites at two positions on the ossicular chain, preferably disposed between the incus and the stapes. Alternatively, attachment means might be disposed at a first site on the temporal bone of the skull and at a second site on the round window. A further possibility is attachment means disposed at a first suitable site on the temporal bone of the skull and at second site on the ossicular chain.

Furthermore, alternative attachment means may be in the form of a block, post or other structure that has been pre-attached to any of the attachment sites immediately hereinbefore described in the preceding paragraph and such alternate attachment means may be used instead of clip means proximally and may also be used distally at the distal end of the piston. In addition, such alternate attachment means may be used in addition to those hereinbefore described. For instance block or post means constituting mounting means might be pre-attached at sites hereinbefore described at respective proximal and distal ends of the actuator and clip or other attachment means integral with the actuator could be subsequently attached to them.

The actuator may be provided with a piston, fixedly attached to the actuator and of such a length that, at implantation, it is brought into gentle pressing contact with preferably but not necessarily the stapes footplate. The piston may be attached to the stapes footplate. Alternatively, the piston may simply contact the stapes footplate. Fixed attachment of the piston to the actuator may be achieved by the use of adhesive means and it is preferable that the long axis of the piston and the long axis of the actuator stack are substantially coaxial. Furthermore it is also preferable that the clip is secured such that the effective axis of operation and the gape of the jaws thereof are arranged substantially at right angles to the shared axis of the actuator and piston. The piston may be made from any one of a number of materials including, non-exclusively, titanium, Teflon™, gold or nitinol or other suitable metals or plastics and it may desirably be in a form such that its length may be adjusted intra-operatively if required or it may also desirably be a standard length which can be cut down as required, or it may be part of a set with different piston lengths. Further means may be used to provide alteration to the effective length of the actuator in order to enable contact and a preloading of the structures to which it is attached. For instance, piston length may be rendered adjustable by means of a sliding element disposed about the distal portion of the piston and retained at the selected position by friction means so as to prevent undesirable migration during acoustic pressure loading. Alternatively, the form of the piston may be adapted so as to be bendable with the aim of providing for length adjustment as might be achieved by, for instance, making it in the form of either a single bendable element or in the form of a shaped frame such as a substantially diamond shaped extendable and compressible frame. A further alternative means for length adjustment is in the form of a miniature screw adjuster.

When suitable metals or alloys or plastics are used to construct the piston it may be extended to provide containment or encapsulation means for the actuator and boss means for the clip. It is also possible when suitable materials are selected, to form the clip integrally with the piston and containment or encapsulation means for the actuator and boss. The purpose of such containment or encapsulation means is to protect the actuator from the internal body environment whilst also isolating the body from the risk of adverse reaction from the actuator materials or the electrical components.

The actuator may be provided with a sound transducer, conveniently in the form of a microphone, which may be located for instance externally in the ear canal or behind the pinna, or internally by implanting it in the pinna or such other site as the surgeon may select.

The actuator may be provided with a sound processor, preferably a digital signal processor (DSP), which may conveniently, but not necessarily, be located with or in close association to the sound transducer to which it is hard wired or wirelessly connected and from which it derives its input signal. The DSP is preferably able to condition sound information contained in the signals detected by the transducer (microphone) such that the profile of hearing loss in each patient may be precisely compensated for at different parts of the hearing spectrum.

The actuator may be provided with a power supply, conveniently a battery, which may be located for instance externally in the ear canal or behind the pinna, or internally by implanting it in the pinna or such other site as the surgeon may select. The power supply provides power to the DSP and, where appropriate, to suitable amplifier means and is preferably hard wired to both of these components. Power supply selection may be from an expendable battery if mounted externally or a very long life implantable battery using technology employed in pacemaker batteries or a rechargeable battery such as an induction coil chargeable device.

Wires may be used to connect the electrical components together. Preferably these wires are very fine and are provided with biocompatible coatings or sheathings. Certain portions of the wiring may pass transcutaneously, subcutaneously or within a bony canal between components.

The middle ear implant components which are to be implanted may be secured together with suitable adhesive means. It may also be necessary to isolate the implantable components from their immediate local environment and this is conveniently achieved by coating with a material such as, by way of non-limiting example only, Parylene™ or some other form of coating Where appropriate, encapsulation coating means which also constitute adhesive means may be used to secure implantable components together as well as to isolate them from their local environment.

Further preferred features and advantages of the present invention will appear from the following detailed description of some embodiments illustrated with reference to the accompanying drawings in which:

FIG. 1 is a schematic right lateral view of an actuator according to a first preferred embodiment of the present invention comprising a piezoelectric component having a stack of piezoelectric elements, a piston element and connecting means for attachment to the ossicular chain of a human or animal patient;

FIG. 2 is a schematic posterior view of the actuator of FIG. 1;

FIG. 3 is a schematic left lateral view of an actuator according to a second preferred embodiment of the present invention comprising a piezoelectric component having a stack of piezoelectric elements, a piston element and connecting means for attachment to the ossicular chain of a human or animal patient wherein extensions of the piston and ossicular attachment means constitute support means substantially surrounding two sides of the piezoelectric component;

FIG. 4 is a schematic posterior view of the actuator of FIG. 3;

FIG. 5 is a schematic perspective view of the actuator of FIG. 3;

FIG. 6 is a schematic left lateral view of a modified version of the actuator of FIG. 3, comprising a piezoelectric component having a stack of piezoelectric elements, a piston element and connecting means for attachment to the ossicular chain of a human or animal patient wherein extensions of the piston and ossicular attachment means constitute side support means substantially surrounding two sides of the piezoelectric component, the side support means being provided with locally modified areas;

FIG. 7 is a schematic right lateral view of an actuator according to a third preferred embodiment of the present invention comprising a piezoelectric component having a stack of piezoelectric elements, a piston element and connecting means for attachment to the ossicular chain of a human or animal patient wherein a coating of the piston, attachment means and piezoelectric component substantially surrounds the entire actuator and thereby providing support means;

FIG. 8 is a schematic posterior view of the actuator of FIG. 7;

FIG. 9 is a schematic perspective view of the actuator of FIG. 7;

FIG. 10 is a schematic view of the actuator of FIG. 7, shown located within the ear of a human patient;

FIG. 11 is a schematic front view of a series of moulded plastic trials for an actuator according to the present invention indicating varying piston lengths;

FIG. 12 is a schematic diagram of the main components of an implantable hearing aid system supporting use of a middle ear implant actuator according to the present invention;

FIG. 13 is a schematic left lateral view of a further preferred embodiment of an actuator according to the present invention, substantially similar to the previous preferred embodiments but having a shorter and more robust piston and alternate locally modified areas to side support means; the stack is omitted in this figure.

The incorporation of suitable electrode means in the actuator of the present invention will be readily apparent to one skilled in the art and, as such, has not been discussed in detail herein.

With general reference to FIGS. 1-12, reference is first made to FIGS. 1 and 2, in which there is shown an actuator 10, for a middle ear implant according to a first preferred embodiment of the present invention.

A middle ear implant is in the form of an electromechanical actuator 10, which comprises a piezoelectric stack 12, desirably having a number of piezoelectric elements which may comprise by way of non-limiting example between 40 and 80, each advantageously though not necessarily being about 0.4 mm by 0.9 mm in cross section and each advantageously though not necessarily being between 20 µm and 40 µm in thickness, and preferably made from lead zirconate titanate (PZT) or other piezoelectric material with equal or better coefficient of transfer from electrical input to mechanical output and arranged, in this embodiment, in d33 configuration and indicated by way of example at 12a, 12b, 12c and 12d. Alternative actuator technologies may also be used with the present invention. For example, the stack may also be constructed and operated in d31 mode. Moreover, in some circumstances a single crystal or other crystalline configuration might be desirable. Alternatively, piezoelectric polymer material may be used.

A piston element 14, is disposed such that the long axes of 12, and of 14, are substantially coaxial and connecting means for attachment to the ossicular chain of a human or animal patient which are in the form of an open jaw clip 16, the 'gape' or entry 16a, of which is arranged substantially at right angles to the coaxial arrangement of 12, and 14. Piston 14, and open jaw clip 16, may be made, conveniently, in suitable materials such as titanium, gold, nitinol, plastics or any other suitable material. Proximal end 18, of 12, is fixedly attached to clip 16, by adhesive means indicated at 20, and which may conveniently be an acrylic polymer. Distal end 22, of 12, is fixedly attached to piston 14, by adhesive means indicated at 24, and which may also conveniently be an acrylic polymer.

It is to be noted that, although the instant invention is herein described with reference to a piezoelectric stack 10, which is oblong in plan view 10, may equally readily be square, or round, or any other convenient shape in plan view.

As may be seen by brief reference to FIG. 10, in use, clip 16, is attached to an ossicle, typically the incus long process 26, and actuator 10, is disposed in such a way that piston 14, is brought to bear gently but firmly on the stapes footplate 28, or in a hole formed therein (not illustrated) by surgical intervention. Actuator 10 may be provided in a series of sizes wherein piston 14 has a different length for each size. Size selection may be assisted by comparison with a series of simple plastic 'trials' described hereinafter with reference to FIG. 11. Alternatively, an over-length piston may be selected and reduced to an appropriate length intra-operatively.

Experiments using a bench rig have shown that when actuator 10, is driven at approximately 5 volts, d33 axial excursions of stack 12, measured with a Polytec® laser vibrometer can exceed 40 nanometers, equivalent to sound pressure levels (SPL) considerably in excess of 100 dB at lower audible frequencies and greater axial excursions may be achieved at higher frequencies.

Experiments using human cadaveric temporal bones have confirmed that when actuator 10, is driven as immediately hereinbefore described, vibration measurements at the stapes footplate similarly equate to an SPL over 90 dB at lower audible frequencies and greater outputs have been achieved at higher frequencies.

Reference is now made to FIGS. 3-6, in which there is shown an actuator 110, for a hearing aid system according to a second preferred embodiment of the present invention.

Actuator 110, comprises a piezoelectric stack 112, having about 50 piezoelectric elements and indicated by way of example at 112a, 112b, 112c and 112d, preferably made from lead zirconate titanate (PZT) and arranged in d33 configuration. A piston element 114, is disposed such that the long axes of 112, and of 114, are substantially coaxial. Connecting means for attachment to the ossicular chain of a human or animal patient are in the form of an open jaw clip 116, the 'gape' or entry 116a, of which is arranged substantially at right angles to the coaxial arrangement of 112, and 114.

Base portion 150, of open jaw clip 116, extends along the whole of first edge 152, of stack 112, and also along the whole of third edge 154, of stack 112, forming first and second side members 156 and 158, respectively. At the distal end 160, of stack 112, first and second side members 156; 158, extend continuously into proximal end 162, of piston 114. It will be appreciated that open jaw clip 116, base portion 150, first and second side members 156; 158, proximal end 162 and piston 114, constitute a single structural entity and may be made in materials such as titanium, gold, nitinol, plastics or any other suitable material. An expansion gap 140, is provided preferably but not necessarily between base support 150, and the proximal end 142, of stack 112, in order to accommodate excursions of stack 112.

It is to be understood that in regard to the function of first and second side members 156; 158, they have no possibility of functioning as flextensional amplifiers. Their presence may be desirable because, when actuators 10, 110, of embodiments of the present invention are driven at the design voltage of 5 volts, excursions of stack 12, of FIGS. 1 and 2, and stack 112, of FIGS. 3-6, may be measured in several tens of nanometers and the provision of first and second side members 156; 158 may contribute significantly to longevity and reliability, both of which are extremely important factors in implanted medical devices.

Nitinol, certain plastics and, to some extent gold, have an inherent capacity for non-plastic deformation and recovery when stressed in the cyclical manner associated with the excursions of piezoelectric stacks used as actuators.

It is also to be noted that, although the instant invention is herein described with reference to a piezoelectric stack 10; 110, which is oblong in plan view 10; 110, may equally readily be square, or round, or any other convenient shape in plan view. In any event, the disposition of first and second side members 156; 158, is preferably on opposite sides of stack 112.

FIG. 6 is a variant of the embodiment of the actuator of FIGS. 3-5, wherein side members 156; 158, have local modified areas 164; 166 extending transversely preferably, though not necessarily, at their respective mid points 168; 170. The form of locally modified areas 164; 166 in cross section is such that substantially triangular shaped zones are enclosed between side members 156; 158, and respective first and third edges 152; 154 of stack 112. Areas 164; 166 are so arranged as to provide substantially unrestricted excursions of actuator 110, in response to amplitudes which are functionally useful in providing hearing augmentation. They may also provide excursion limiting or attenuating means in the event of very large excursions which might occur in response to high energy signals, such as transient sound signals, in conjunction with the high driving voltage of the device.

FIGS. 7-9 illustrate an actuator 210, according to a third preferred embodiment of the present invention comprising a piezoelectric stack 212, a piston element 214, and connecting means comprising clip means 216, for attachment to the ossicular chain of a human or animal patient.

Elements 212, 214 and 216, are seen in outline only by virtue of a coating 272, which substantially surrounds the entire actuator 210, including stack 212, piston element 214, and clip 216, constituting containment (or encapsulation) and sealing means. Coating 272, is resilient and is sufficiently stiff and has sufficient strength and structural integrity to constitute casing means surrounding entire actuator 210.

The proximal end of stack 212, is fixedly attached to clip 216, by adhesive means (not seen) which may conveniently be an acrylic polymer. The distal end of 212, is fixedly attached to piston 214, by adhesive means (not seen) which may also conveniently be an acrylic polymer.

Coating 272, may be made of the same material as adhesive means used to secure piston 214, and clip 216, to stack 212, or may be made of a different material, in any event is it important that coating 272, is made from biocompatible material.

It is further to be noted that, although the instant invention is herein described with reference to a piezoelectric stack 210, which is oblong in plan view, 210 may equally readily be square, or round, or any other convenient shape in plan view.

Note that coating 272, is not the direct equivalent of a proprietary coating used for shielding surgical implant materials from biohazards, rather it is a structural component. However, it is desirable that a biocompatible ultra thin layer outer layer of a material such as Parylene® is used to protect the body from the implant and vice versa from toxic or other undesirable agents.

In FIG. 13 there is shown a schematic left lateral view of another preferred embodiment of an actuator frame 310, which embodies the present invention, substantially similar to variant 110, of the embodiment of the actuator of FIGS. 3-5, and 6, but having a shorter and more robust piston 316, and alternate locally modified areas 364; 366, to side members 356; 358, located proximally rather than at the midpoints for the accommodation of stack excursions (the stack is omitted in FIG. 13). This embodiment may be preferred when very high driving voltages are employed.

All embodiments of the present invention immediately hereinbefore described are deployed at surgery in substantially the same manner by introducing the gape 16a; 116a; 216a, 316a, of clip 16; 116; 216, 316, respectively, to the incus long process and gently pushing it to cause opening and subsequent engagement, location and closing of clip 16; 116; 216, 316. This procedure may be aided by using a suitable instrument to gently prise open the clip 16, 116, 216, 316. However, it is to be understood, by non-surgeons and surgeons alike, that the entire device 10, 110, 210, 310 is extremely small, measuring usually no more than 5.5 mm in length (and generally less) and concomitantly clip 16, 116, 21616, 116, 216, 316 is designed to surround an ossicle of ovoid cross section likely to be no more than 0.7 mm in one direction and 0.9 mm in a second direction and will inevitably be extremely small and delicate, no matter from what material it may be made. Reference to FIG. 10, shows the middle ear implant in situ in the ear of a patient.

Pistons 14; 114; 214, 314 may require to be provided in differing lengths for different patients whose anatomy varies in a more or less known but unpredictable (pre-surgery) basis. Accordingly, a supplier supplying a surgeon user with actuators 10; 110; 210, 310 in different lengths may assist by also supplying trials 80, as illustrated in FIG. 11. Trials 80, are conveniently moulded in suitable plastics by injection moulding and are supplied sterilised. Trials 80, comprises representations indicated at 82, 84, 86, 88, 90, 92, 94, in moulded plastics of all available sizes of actuator 10; 110; 210, 310 in the suppliers exemplary range, each size being clearly indicated, for example by being provided with numerical information moulded into the body of trials 80, as exemplified at 96, and secured by a very small breakable tag indicated at 98. At surgery, and with the target site exposed and prepared, trials 80, is removed from its sterile packaging, usually by an assistant to the surgeon and a selected size is grasped in small surgical tweezers, wrested free from tag 96, and carefully offered up to the surgical site to establish the appropriateness of that size or otherwise, by a relatively swift process of trial and error, the optimum size of 10; 110; 210, 310 may be selected and implanted.

Under an alternative regime, piston 14; 114; 214; 314 may be deliberately selected over-length and trimmed down to the required size intra-operatively.

Referring to FIG. 12, there is illustrated, in schematic form, a suitable arrangement for use of the middle ear prosthesis of the present invention, specifically mechanical actuator 10; 110; 210; 310 in a partially implantable hearing aid system 11. Microphone 13, may conveniently be situated in the ear canal 15, and its output directed by connecting wires, generally indicated at 17; 17a, to a DSP which, together with appropriate ancillary circuitry, is indicated at 19, and an amplifier 21, located in a housing 23, and which may conveniently be placed behind the ear 25, of a patient. Housing 23, (shown out of its in-use resting position for clarity) also conveniently provides housing means for at least one battery 27. Battery 27, provides power to DSP and circuitry 19, amplifier 21, and to stack 12; 112; 212, of actuator 10; 110; 210, respectively. Electrical connection conveying output from DSP and circuitry 19, and amplifier 21, to stack 12; 112; 212; 312 of actuator 10; 110; 210, is achieved using connecting wires 17; 17a, which are run in a surgically created tunnel indicated diagrammatically at 29, extending medially from a point close to the superior origin of the pinna 31, subcutaneously and where appropriate sub-periosteally and trans-osteally to a point within the middle ear space 33, slightly anterior of the lateral aspect of the malleus from whence 17; 17a emerge, thereafter extending to connect with stack 12; 112; 212.

DSP 19, may be operated at up to 2.5 volts DC or more, depending upon its type and model and battery 27 is selected so as to provide this. The output from 19, may foe input to amplifier 21, and the output from 21, conveniently employed to drive actuator 10; 110; 210; 310.

Although several preferred embodiments of the present invention have been described in the foregoing detailed description, it is to be understood that the invention is not limited to those embodiments disclosed herein but is capable of numerous rearrangements, modifications and substitutions without departing from the scope of the invention as set forth and defined by the following claims.

In particular, the above described embodiments have a piston which has a substantially fixed length. However, in other embodiments, the length may be adjustable. For example, the piston may have two or more relatively slidable parts, whose relative position can be adjusted to a desired length when the actuator is implanted, but which can subsequently be fixed in position so that they do not move relative to one another during use. Alternatively, the friction between the slidable parts may be sufficient to prevent relative movement thereof under the action of the transducer, whilst allowing for relative movement thereof by a surgeon when the device is implanted.

Alternatively, the length of the piston may be adjusted using screw adjustment means.

Further alternatively, the piston may be formed of four elements connected together in a diamond configuration, wherein the piston is bendable at these connections. Thus, the length of the piston can be increased by decreasing the width of the diamond shape, and vice versa. Further configurations of pistons whose length is adjustable by means of bendable connections, or bendable sections are also envisaged. For example, a bendable strut.

In these cases, the longitudinal axis of the piston remains substantially parallel to that of the transducer element, irrespective of how the piston is bent. This is the case even though, in some configurations, there may be no structural element which extends along the longitudinal axis. Accordingly, in all cases, the line of action of the piston remains substantially parallel with (and preferably coaxial with) that of the transducer means.

Once adjusted to a desired length, the bendable portions may be stiffened to prevent further adjustment of the length. Alternatively, the stiffness of the bendable portions could be sufficient to prevent the action of the transducer having any substantial affect on the length of the piston during use.

The above described embodiments have attachment means in the form of a jaw clip. However, any suitable form of clip or gripping means may be used. Alternatively, or in addition, bio-compatible/bioactive adhesive or cement such as ionomeric cement may be used.

The piston (contacting means) may also be attached to the desired part of the middle ear, although in certain embodiments it may simply contact that part of the middle ear without being attached thereto. In cases where the piston is attached, this may be achieved by means of biocompatible/bioactive adhesive or cement, or by means of a clip or other gripping means.

In the above described embodiments, the actuator is intended to be attached at one end to the incus long process, such that the other end of the device comes into contact with (and may be attached to) the stapes footplate. However, as discussed in more detail above, the actuator may also be configured to extend between other combinations of points within the middle ear. In this respect, it is preferred that the actuator extends from a first part of the middle ear that is not fixed relative to a second part thereof. More specifically, it is preferred that the actuator extends from a point on one element of the middle ear, to a point on a different element of the middle ear. That is to say, it will preferably extend from a point on the temporal bone to a point on one of the ossicles or to the round window. Alternatively, it may extend from a point on one of the ossicles to a point on a different ossicle, or to the temporal bone, or to the round window.

Certain of the above described embodiments are shown with side walls in contact with the piezoelectric stack. In practice, a narrow gap may be present between the side walls and the stack.

In certain of the above described embodiments, the side walls have local deformations which effectively make the length of the side walls adjustable, so as to accommodate the vibrations of the transducer means. However, alternative ways of making the length of the side walls adjustable are envisaged. For example, the side walls may have two or more elements which are joined together by a seal means which is formed of a resilient or stretchable material.

The invention claimed is:

1. A hearing actuator for implantation in a middle ear of a user, the actuator comprising:
   a transducer to convert electrical input signals into mechanical vibrations comprising changes in the length of the transducer along a longitudinal axis;
   an attachment member fixedly attached to a first end of the transducer to directly attach the first end of the transducer to an incus; and
   a piston element to extend away from an opposite second end of the transducer such that a longitudinal axis of the piston element is substantially parallel to said longitudinal axis of the transducer, and such that, when the actuator is implanted in the middle ear with said first end of the transducer attached to the incus, the piston element contacts a stapes footplate, or extends through a hole formed in the stapes footplate,
   wherein the changes in the length of the transducer along a longitudinal axis cause the piston element to vibrate, thereby transmitting said mechanical vibrations of the transducer to the stapes footplate or through the hole in the stapes footplate via the piston element.

2. A hearing actuator as claimed in claim 1 wherein the piston element has an elongate form.

3. A hearing actuator as claimed in claim 1 wherein the longitudinal axis of the transducer and the longitudinal axis of the piston element are substantially aligned on a common axis.

4. A hearing actuator as claimed in claim 1 wherein the attachment member is configured to attach to a mounting member that has been pre-attached to a respective point within the middle ear.

5. A hearing actuator as claimed in claim 1 wherein one or both of the piston element and the attachment member is integrally formed with side walls which extend around at least one side of the transducer.

6. A hearing actuator as claimed in claim 5 wherein each side wall comprises a resiliently extendible portion which allows the side walls to expand and contract with said mechanical vibrations of the transducer.

7. A hearing actuator as claimed in claim 1 wherein the piston element comprises two or more sections connected together, wherein the piston element is bendable at said connections for adjusting the length of the piston element.

8. A hearing actuator as claimed in claim 7 wherein the piston element comprises four of said sections arranged in a diamond configuration.

9. A hearing actuator for implantation in a middle ear of a user, the actuator comprising:
   a transducer to convert electrical input signals into mechanical vibrations comprising changes in the length of the transducer along a longitudinal axis;
   a mounting member attachable to a site on a temporal bone within the middle ear of the user;
   an attachment member fixedly attached to a first end of the transducer to directly attach the first end of the transducer to the mounting member on said site on the temporal bone; and
   a piston element, which extends from an opposite second end of the transducer such that a longitudinal axis of the piston element is substantially parallel to said longitudinal axis of the transducer, and such that, when the actuator is implanted in the middle ear with said first end of the transducer attached to said site on the temporal bone via the attachment member and the mounting member, the piston element contacts a round window, wherein the changes in the length of the transducer along a longitudinal axis cause the piston element to vibrate, thereby transmitting said mechanical vibrations of the transducer to the round window via the piston element.

10. A hearing actuator as claimed in claim 9 wherein the piston element has an elongate form.

11. A hearing actuator as claimed in claim 9 wherein the longitudinal axis of the transducer and the longitudinal axis of the piston element are substantially aligned on a common axis.

12. A hearing actuator as claimed in claim 9 wherein the attachment member is configured to attach to a mounting member that has been pre-attached to a respective point within the middle ear.

13. A hearing actuator as claimed in claim 9 wherein one or both of the piston element and the attachment member is integrally formed with side walls which extend around at least one side of the transducer.

14. A hearing actuator as claimed in claim 13 wherein each side wall comprises a resiliently extendible portion which allows the side wall to expand and contract with said mechanical vibrations of the transducer.

15. A hearing actuator as claimed in claim 9 wherein the piston element comprises two or more sections connected together, wherein the piston element is bendable at said connections for adjusting the length of the piston element.

16. A hearing actuator as claimed in claim 15 wherein the piston element comprises four of said sections arranged in a diamond configuration.

17. A method of surgically implanting a hearing actuator, the method comprising inserting the actuator recited in claim 9 into the middle ear via the ear canal and incised and folded back eardrum, and attaching an attachment means of the actuator to a first desired point in the middle ear, such that a contacting means of the actuator contacts a second desired point in the middle ear.

18. A method as claimed in claim 17 further comprising the step of attaching the contacting means to said second desired point.

19. A method as claimed in claim 17 further comprising determining an appropriate size of actuator for a patient, using a series of trial devices of different sizes, corresponding to available sizes of actuator.

20. A method as claimed in claim 17 further comprising selecting an over-sized actuator and modifying the actuator to achieve a desired size.

21. A method as claimed in claim 17 further comprising the step of attaching a mounting member to a desired point in the middle ear of the patient, and subsequently attaching the attachment means of the actuator to the mounting means.

22. A method as claimed in claim 17 further comprising the step of adjusting the length of the contacting means such that the contacting means contacts said second desired point in the middle ear.

* * * * *